United States Patent [19]
Adkins, Jr. et al.

[11] Patent Number: 5,392,775
[45] Date of Patent: Feb. 28, 1995

[54] DUCKBILL VALVE FOR A TRACHEOSTOMY TUBE THAT PERMITS SPEECH

[76] Inventors: Claude N. Adkins, Jr., 3425 Westminster Ave., Monroe, La. 71202; Blane P. Marie, 137 Liner Dr., Monroe, La. 71203

[21] Appl. No.: 216,172

[22] Filed: Mar. 22, 1994

[51] Int. Cl.⁶ .................... A61M 16/20; A61M 16/04; A62B 9/02; A61F 2/20
[52] U.S. Cl. .................. 128/207.16; 623/9; 128/207.14
[58] Field of Search ............ 128/207.14, 207.15, 128/207.16, 207.29, 911, 912; 623/9

[56] References Cited

U.S. PATENT DOCUMENTS

| | | | |
|---|---|---|---|
| 3,137,299 | 6/1964 | Tabor | 128/351 |
| 3,952,335 | 4/1976 | Sorce et al. | 128/207.16 |
| 3,993,624 | 9/1972 | Shiley et al. | 128/351 |
| 4,029,105 | 6/1977 | Faust | 128/351 |
| 4,040,428 | 8/1977 | Clifford | 128/351 |
| 4,325,366 | 4/1982 | Tabor | 128/207.16 |
| 4,416,273 | 11/1983 | Grimes | 128/207.16 |
| 4,506,665 | 3/1985 | Andrews et al. | 128/202.27 |
| 4,513,741 | 4/1985 | Demi | 128/205.25 |
| 4,614,516 | 9/1986 | Blom et al. | 623/9 |
| 4,759,356 | 7/1988 | Muir | 128/207.16 |
| 4,774,945 | 10/1988 | White et al. | 128/207.16 |
| 4,909,248 | 3/1990 | McLennan Anderson | 128/207.14 |
| 4,971,054 | 11/1990 | Ansersson et al. | 128/207.16 |
| 5,048,518 | 9/1991 | Eliachar et al. | 128/207.14 |
| 5,123,922 | 6/1992 | Berg | 623/9 |

OTHER PUBLICATIONS

Passy-Muir, Inc., *Tracheostomy Speaking Valves*, ©1989, Irvine, Calif., 92715 (1-800-634-5397).

*Primary Examiner*—Kimberly L. Asher
*Assistant Examiner*—William J. Deane, Jr.
*Attorney, Agent, or Firm*—Robert C. Tucker; William David Kiesel

[57] ABSTRACT

A tracheostomy valve for use in conjunction with a tracheostomy tube is described. The tracheostomy valve comprises a housing and a one-way valve. The housing has an aperture including a forward and rear opening defined therethrough. The housing also includes a rear portion proximate the rear opening adapted to sealingly connect the rear opening with a tracheostomy robe. The one-way valve is mounted to the homing in operational connection between the forward and rear openings of the aperture. The one-way valve includes a flexable portion, having a surface area greater than the cross-sectional area of the aperture through the housing, which comprises first and second flexible edges. The first and second flexable edges are arranged in a manner such that the first and second flexible edges are biased into sealing contact when the air pressure within the rear opening is greater than the air pressure in the forward opening, and biased out of sealing contact when the pressure within the rear opening is less than the air pressure within the forward opening. The flexable portion is adapted to deformably extend through the forward opening by the pressure created during a cough.

9 Claims, 3 Drawing Sheets

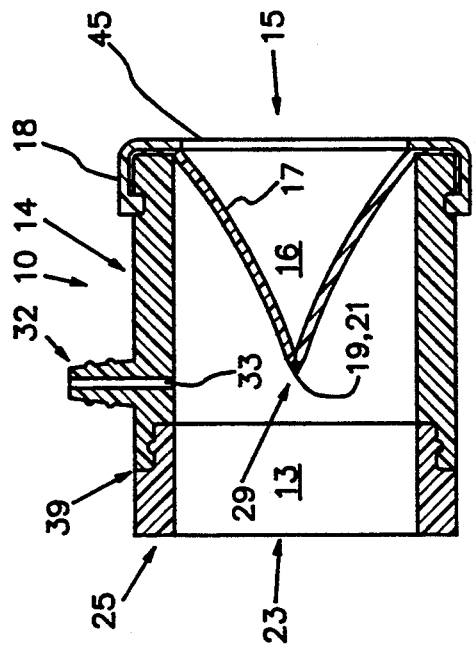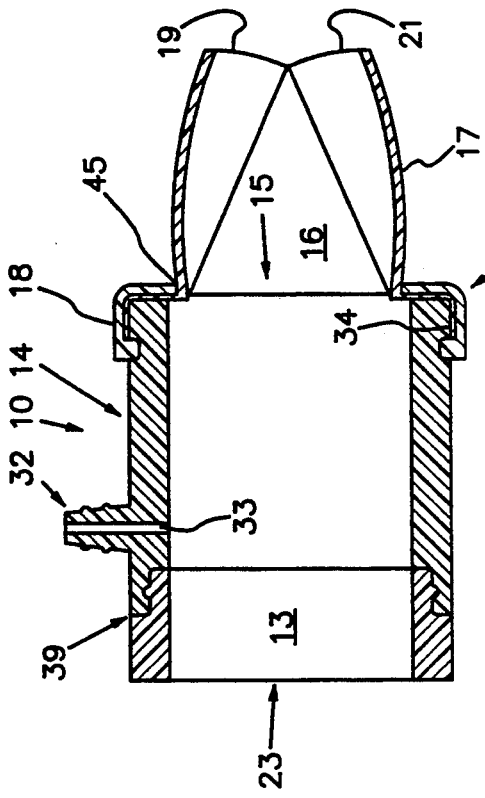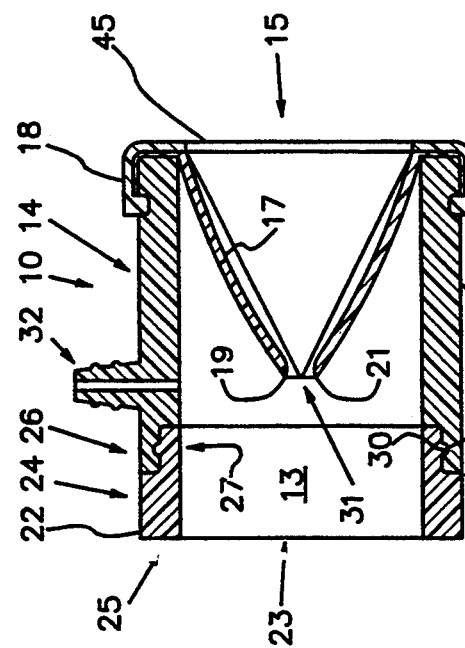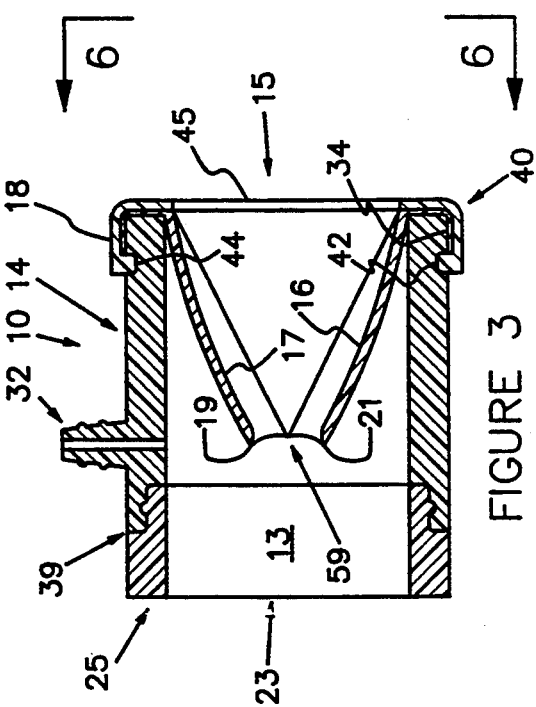

DUCKBILL VALVE FOR A TRACHEOSTOMY TUBE THAT PERMITS SPEECH

FIELD OF THE INVENTION

The present invention relates to tracheostomy valves and, more particularly, to tracheostomy valves that block the outward passage of air during normal conversation but allow the outward passage of air during a cough.

GENERAL BACKGROUND

Patients suffering from chronic obstructive pulmonary diseases and neuro-muscular diseases often require support ventilation while sleeping in order to prevent the occurrence of carbon dioxide narcosis. This type of ventilation generally requires the installation of a tracheostomy tube. Because the tracheostomy tube remains in place during the day, it is generally desirable to attach a one-way, or speaking valve, to the outward end of the tracheostomy tube. The valve allows the patient to carry on conversations.

Patients complain that the speaking valves are uncomfortable because of the initial effort required to bias the valve open at the beginning of each inhalation. This increased effort can exhaust the patient. Mucus contamination of the valve can significantly increase the effort required to bias the valve open.

The typical speaking valve consists of a flexible disc-shaped diaphragm that collapses inward upon inhalation and seals against a fixed surface upon exhalation. There are two variations of this type valve. In the first variation, of which the description in U.S. Pat. No. 3,137,299 to Tabor is exemplary, the disc-shaped diaphragm is attached to the valve housing through its center. In the second variation, the disc shaped diaphragm is attached to the valve housing along one edge. U.S. Pat. No. 4,040,428 to Clifford is exemplary of this variation.

Valve sticking can become a problem with these types of valves because, as mucus accumulates, the flexible diaphragm can become tacky and begin to adhere to the fixed surface during each exhalation. Since the diaphragm is now adhering to the fixed surface, the patient must expend more force inhaling to create a vacuum in the conduit of the valve housing which is sufficient to free the edge of the diaphragm from the fixed surface. This can become very uncomfortable after even a short period of time. It would be desirable, therefore, to have a tracheostomy valve which would require less inhalation effort to bias open even when the seal becomes tacky.

In addition, the fixed surface which forms part of the sealing mechanism is located adjacent the inner surface of the conduit portion of the typical speaking valve housing. This means that there is a greater likelihood of mucus accumulation on or near the sealing surfaces of the valve. It would be desirable, therefore, to have a tracheostomy valve which would have the sealing surfaces located within the conduit portion of the valve housing at a location away from the inner surface of the conduit, thereby minimizing the accumulation of mucus on the sealing surfaces.

Also, because the typical speaking valve has a fixed surface as a part of its sealing mechanism, only one force acts to separate the surfaces when they begin to adhere. The force acts against the diaphragm and is directly proportional to the pressure differential between the ambient atmosphere and the vacuum created in the valve housing conduit by the expanding lungs, and the surface area of the diaphragm. In order to generate a greater opening force, it is necessary to either increase the surface area of the diaphragm or increase the pressure differential between the ambient atmosphere and the valve housing conduit. Since it is desired to open the valve with the smallest pressure differential possible, it is desirable to have a tracheostomy valve which includes force generating surfaces which have a surface area greater than the cross-sectional area of the valve housing conduit. It would be an additional benefit if a second force were generated which acts conjunction with the first force to open the valve.

SUMMARY OF THE INVENTION

Therefore, it is an object of the present invention to provide a tracheostomy valve which will allow the patient to talk but which requires very little pressure differential to bias into the open position.

It is a further object of the present invention to provide a tracheostomy valve which includes force generating surfaces which have a surface area greater than the cross-sectional area of the valve housing conduit.

It is a still further object of the present invention to provide a tracheostomy valve which will generate dual separation forces during the opening stage of the valve operation.

It is yet another object of this invention to provide a tracheostomy valve which allows an outward passage of air during a cough, but is easily reset by the user to a normal operating position.

Accordingly, a tracheostomy valve for use in conjunction with a tracheostomy tube is described. The tracheostomy valve comprises a housing and a one-way valve. The housing, preferably constructed of plastic, has an aperture including a forward and rear opening defined therethrough. The housing also includes a rear portion, proximate the rear opening, adapted to sealingly connect the rear opening with a tracheostomy tube. The one-way valve is mounted to the housing in operational connection between the forward and rear openings of the aperture. The one-way valve, preferably a duckbill valve, includes a flexible portion, having a surface area greater than the cross-sectional area of the aperture through the housing, which comprises first and second flexible edges. The first and second flexible edges are arranged in a manner such that the first and second flexible edges are biased into sealing contact when the air pressure within the rear opening is greater than the air pressure in the forward opening, and biased out of sealing contact when the pressure within the rear opening is less than the air pressure within the forward opening. The flexible portion is adapted to deformably extend through the forward opening by the pressure created during a cough. In another embodiment, the first and second flexible edges of the valve are biased apart when the pressure within the rear opening is substantially equal to the pressure within the forward opening.

In another embodiment, the housing has a side opening in fluid communication with the housing aperture at a location between the rear opening and the flexible portion, and the tracheostomy valve further includes a fitting having a first end, a second end, and a fitting aperture defined therethrough. The fitting aperture is in connection between the first and second ends. The first end of the fitting is sealingly installed within the side opening in a manner such that the fitting aperture is in connection with the housing aperture. The second end of the fitting has an outer portion adapted for connection with an oxygen source. The housing may include a means for allowing a portion of the housing containing the side opening to rotate in relation to the tracheostomy tube. Alternatively, the housing may includes means for allowing a portion of the housing containing the side opening to rotate in relation to the rear opening.

A retaining cap may be provided to fix the position of the one-way valve in the forward end of the housing. The retaining cap is provided with a retaining cap opening alignable with the housing aperture.

BRIEF DESCRIPTION OF THE DRAWINGS

FIG. 2 is a cross-sectional view of an embodiment of the tracheostomy valve in a neutral state caused by equal air pressure within the forward and rear openings.

FIG. 3 is a cross-sectional view of the embodiment of the tracheostomy valve shown in FIG. 2 in operation during inhalation.

FIG. 4 is a cross-sectional view of the embodiment of the tracheostomy valve shown in FIG. 2 in operation during normal exhalation and speech.

FIG. 5 is a cross-sectional view of the embodiment of the tracheostomy valve shown in FIG. 2 in operation after a cough has occurred.

DETAILED DESCRIPTION OF PREFERRED EMBODIMENTS OF THE INVENTION

Figure 1:
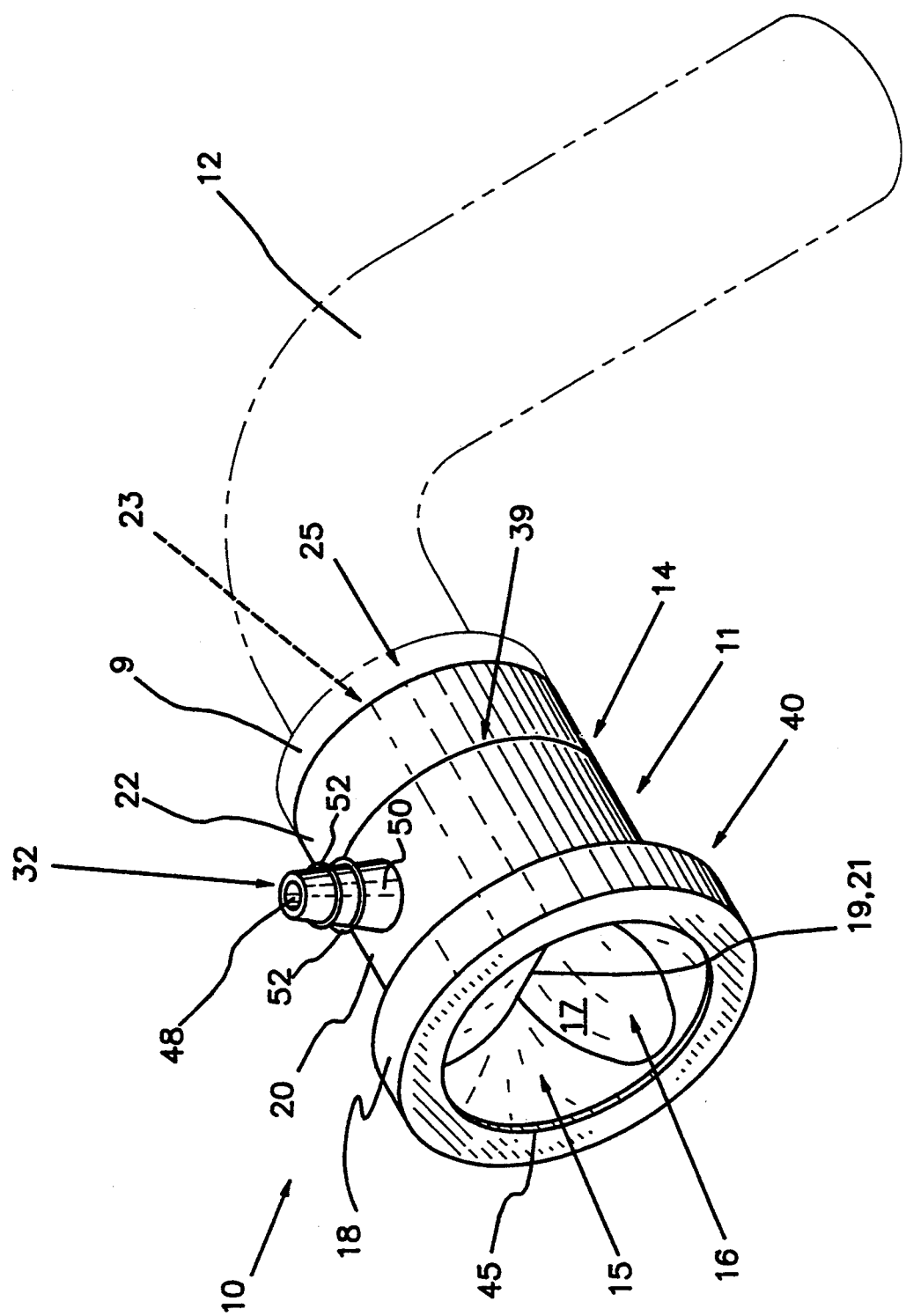
FIG. 1 is an isometric view of an embodiment of the tracheostomy valve of the present invention in connection with a representative tracheostomy tube.

A preferred embodiment of the tracheostomy valve of the present invention, generally indicated by the numeral 10, is shown in FIG. 1 in connection with a representative tracheostomy tube 12. The preferred embodiment of the tracheostomy valve 10 comprises a valve housing, generally indicated by the numeral 14, a one-way valve 16, and a retaining cap 18.

As shown in FIG. 1, the valve housing 14 comprises a plastic tubular shaped section 11 having a longitudinal aperture 13 (see FIGS. 2-5) connecting a forward opening 15 and a rear opening 23. The rear end 25 of the valve housing 14 is adapted to allow connection with a tracheostomy tube 12. In this embodiment the internal diameter of rear opening 23 is selected to correspond with the outer diameter of the end 9 of the tracheostomy tube 12.

As shown in the Figures, one-way valve 16, having a flexible portion 17 which includes two flexible edges 19,21 which define an air flow passage 59 through flexible portion 17, is preferably an elastic duckbill valve having a flexible portion 17 with a surface area greater than the cross-sectional area of the longitudinal aperture 13. The one-way valve 16 is mounted to housing 14 in operational connection between the forward opening 15 and rear opening 23. The term "operational connection" is used herein to mean capable of blocking the flow of air out through the forward opening 15. When the air pressure within the rear opening 23 of the valve housing 14 is greater than the ambient atmospheric air pressure, as when exhaling, the flexible edges 19,21 are forced together forming a seal 29 (see FIG. 4) which closes air flow passage 59 and prevents the flow of air out through the forward opening 15. When the ambient air pressure is greater than the pressure within the rear opening 23, as when inhaling, the flexible edges 19,21 are forced apart (see FIG. 3) allowing air to flow in through the forward opening 15 and out through the rear opening 23. When the pressure within the forward 15 and rear opening 23 is equal flexible edges 19,21 may be either contacting each other or slightly parted (see FIG. 2). It is preferred the during such a resting position the distance between flexible edges 19,21 be between 0.5 and 2 millimeters, more preferably between 0.75 and 1.5 millimeters, and most preferably be about 1 millimeter. This may be accomplished by selecting the size of the duckbill valve 16 to be slightly smaller than the internal diameter of the longitudinal aperture 13. Thus, when the duckbill valve 16 is stretched across forward opening 15, edges 19,21 will be biased slightly apart in resting position 31, shown in FIG. 2, further discouraging edges 19,21 from adhering together. The flexible portion 17 of the duckbill valve 16 is sufficiently flexible to allow the flexible portion 17 to be inverted and partially forced through the forward opening 15 in the event the patient coughs while the tracheostomy valve 10 is in use, as shown is FIG. 5.

It is preferred that tracheostomy valve 10 include a means 39 for allowing a portion of housing 14 to rotate in relation to the remainder of housing 14 or in relation to tracheostomy tube 12. As shown in FIG. 2, means 39 may include an embodiment wherein valve housing 14 includes two tubular shaped plastic sections including a forward section 20 having a forward opening 15 and a rear section 22 having a rear opening 23. In this embodiment the forward and rear sections 20,22 are attached by a snap connector, generally indicated by the numeral 24, which allows the forward section 20 to rotate with respect to the rear section 22.

The snap connector 24, in this preferred embodiment, consists of a circumferential recess 28, formed on one end 26 of the forward section 20, and a companionately dimensioned and located circumferential ridge 30, formed on one end 27 of the rear section 22. The forward and rear sections 20,22 are rotatably connected to allow the oxygen fitting 32 to tie rotated into a desired position during use. Although the circumferential ridge 30 is located on the rear section 22 and the circumferential recess 28 is located on the forward section 20 in this embodiment, the location of either recess 28 or ridge 30 of the snap connector 24 on any particular housing section is not required to practice this embodiment of the invention. It is preferred that a portion of the housing 14 which includes the oxygen fitting 32 is rotatable in relation to either the tracheostomy tube 12 or the rear opening 23.

With reference to FIG. 3, the forward end 40 of housing 14 is preferably adapted to allow connection of retaining cap 18. One-way valve 16 includes a flexible lip portion 34 extending exterior of forward end 40 of housing 14. Retaining cap 18 is connected to forward end 40 so as to fix lip portion 34 between retaining cap 18 and housing 14. In this embodiment an exterior circumferential groove 42 is provided in forward end 40 of the housing 14. The circumferential groove 42 is dimensioned to correspond to the dimensions of a lipped portion 44 which is formed on the retaining cap 18. Retaining cap 18 includes a retaining cap opening 45, aligned with longitudinal aperture 13 and preferably having a diameter which is greater than the diameter of the longitudinal aperture 13. By selecting the diameter of the retaining cap opening 45, within a range between the internal diameter of the longitudinal aperture 13 and the external diameter of the valve housing 14, the pressure required to invert the one-way valve 16 may be adjusted. Within this range of diameters, as the diameter of the retaining cap opening 45 becomes larger the pressure required to invert the flexible portion 17 of the one-way valve 16 becomes less. Although this preferred embodiment includes a retaining cap 18 having a lipped portion 44, the retaining cap 18 is not necessary to practice the invention. One-way valve 16 must simply be maintained in operational connection between forward opening 15 and rear opening 23 of the valve housing 14. This may be accomplished in any manner well known in the art such as with glue, a compression band, or a stretched fitting of lip portion 34 of one-way valve 16 around forward end 40.

Figure 7:
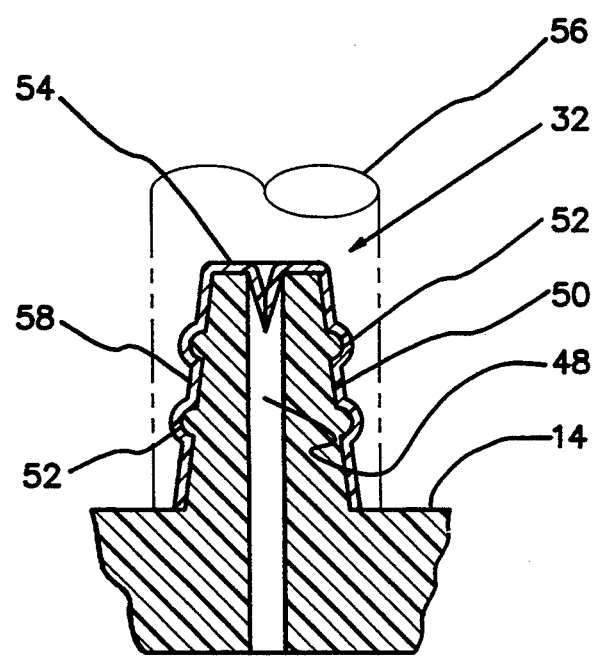
FIG. 7 is a enlarged cross-sectional detail view of an embodiment of the oxygen fitting of the invention having a one-way valve in connection with a typical plastic oxygen tube.

With reference to FIGS. 4 and 7, a preferred oxygen fitting 32 is described. The oxygen fitting 32 includes a fitting aperture 48 which is in fluid connection with the longitudinal aperture 13 of the valve housing 14 via side opening 33. The outer portion 50 of the oxygen fitting 32 is frusto-conical in shape and has two retaining ridges 52. The retaining ridges 52 help maintain connection between the oxygen fitting 32 and a flexible oxygen line 56. Although a preferred oxygen fitting 32 is frusto-conical in shape and is integrally formed with the forward section 20 of the valve housing 14, the oxygen fitting 32 may be substantially tubular in shape, may be constructed separately and may be attached to the valve housing 14 by any well known method such as providing an aperture through the forward section 20 and gluing the oxygen fitting 32 into place.

FIG. 7 shows another preferred embodiment of the oxygen fitting 32 which includes a one-way valve 54, similar in construction to one-way valve 16. The one-way valve 54 closes to allow the tracheostomy valve 10 to be used when it is not desired to install the oxygen line 56. In this embodiment, the one-way valve 54 is an elastic duckbill valve which has a portion 58 placed over the outer portion 50 of the oxygen fitting 32 and is held in place by the oxygen line 56. Although the one-way valve 54 is installed in the foregoing manner, any one-way valve 54 may be installed in the oxygen fitting 32 in any manner which allows the one-way valve 54 to operate as described.

In use, the tracheostomy valve 10 of the present invention is connected to a tracheostomy tube 12 which has been inserted into the trachea of a patient. As previously described, proper function of the tracheostomy valve 10 requires (i) the free passage of air through the tracheostomy valve 10 during the inhalation portion of the normal breathing cycle, (ii) the blockage of the passage of air through the tracheostomy valve 10 during the exhalation portion of the normal breathing cycle, and (iii) the passage of air through the tracheostomy valve 10 during coughing episodes. FIGS. 2–6 illustrate operation of a preferred embodiment of the tracheostomy valve 10.

FIG. 2 shows the position of the flexible edges 19,21 of the one-way valve 16 in their normal resting position 31. The flexible edges 19,21 assume this position when the pressure in the forward and rear openings 15,23 is substantially equal. This pressure condition corresponds to the patient holding his breath.

Figure 6:
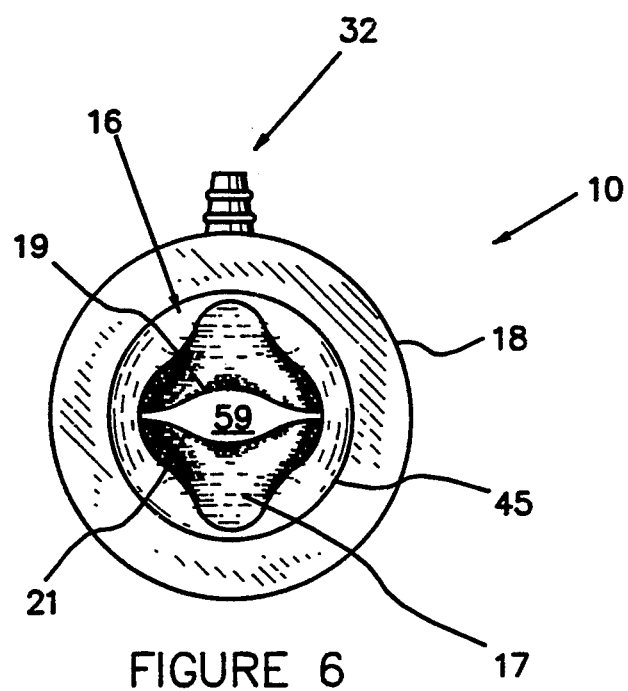
FIG. 6 is a frontal view of the embodiment of the tracheostomy valve shown in FIG. 3 along view line 6—6 which shows the valve in operation during normal inhalation.

FIG. 3 illustrates the position of the flexible edges 19,21 of the one-way valve 16 during the inhalation portion of the normal breathing cycle. As shown, the greater pressure in the forward opening 15 during inhalation forces the flexible edges 19,21 apart, allowing air to pass freely through the tracheostomy valve 10 into the tracheostomy tube 12. FIG. 6 is a front view of FIG. 3 along the line 6—6. FIG. 6 more clearly shows the air-flow passage 59 created for air flow during this portion of the normal breathing cycle and operation of the flexible portion 17.

FIG. 4 illustrates the position of the flexible edges 19,21 of the one-way valve 16 during the exhalation portion of the normal breathing cycle. As shown, the greater pressure in the rear opening 23, created during exhalation and during normal speaking forces the flexible edges 19,21 together so as to form a seal 29, preventing the flow of air through the tracheostomy valve 10, diverting the air up through the larynx for speech.

FIG. 5 illustrates the position of the flexible portion 17 of the one-way valve 16 just after a cough or other violent expulsion of air from the lungs has occurred. As shown, the one-way valve 16 becomes inverted and forced through the retaining cap opening 45. When the one-way valve 16 is in this condition, the flexible edges 19,21 are forced apart allowing air to flow freely in either direction through the tracheostomy valve 10.

The valve 10 may be easily reset from an inverted position to its normal position by pressing the flexible portion 17 back into the valve housing 14 or by forcefully inhaling. The valve 10 also facilitates aspiration or other operations requiring devices to be inserted into or through the tracheostomy tube 12. Flexible portion 17 opens to admit such devices without removing the valve 10 from the tracheostomy tube 12.

It is to be understood that the preceding description is of the preferred embodiment and that various modifications and changes may be made thereto without departing from the spirit and scope of the invention as defined in the following claims.

What is claimed is:

1. A tracheostomy valve for use in conjunction with a tracheostomy tube, said tracheostomy valve comprising;

a valve housing having an aperture including a forward and a rear opening defined therethrough, said housing having a rear end proximate said rear opening adapted to sealingly connect said rear opening with a tracheostomy tube and a forward end proximate said forward opening;

a one-way valve, mounted to said housing in operational connection between said forward and rear openings of said aperture, said one-way valve comprising a duckbill valve having a flexible portion with a surface area greater than the cross-sectional area of said aperture through said housing, said flexible portion including first and second flexible edges defining an air flow passage through said flexible portion, said first and second flexible edges being biased into sealing contact and closing said air flow passage responsive to exhalation, wherein the air pressure within said rear opening is greater than the air pressure in said forward opening, and biased out of sealing contact and opening said air flow passage responsive to inhalation, wherein the pressure within said rear opening is less than the air pressure within said forward opening, said flexible portion deformably extending through said forward opening responsive to pressure created during a cough.

2. The tracheostomy valve of claim 1, wherein said housing further includes a side opening, in fluid communication with said aperture at a location between said rear opening and said flexible portion, and a fitting having a first end, a second end, and a fitting aperture defined therethrough, said fitting aperture being in connection between said first and second ends, said first end of said fitting being in fluid connection with said side opening wherein said fitting aperture is in fluid connection with said aperture of said housing, said firing having an outer portion adapted for connection with an oxygen source.

3. The tracheostomy valve of claim 1, wherein said housing includes a means for allowing a portion of said housing to rotate in relation to a tracheostomy tube.

4. The tracheostomy valve of claim 1, wherein said housing includes a means for allowing a portion of said housing containing said side opening to rotate in relation to the remainder of said housing.

5. The tracheostomy valve of claim 1, wherein said one-way valve further includes a lip portion extending exterior of said forward end of said housing, said tracheostomy valve further comprising a retaining cap connected to said forward end of said housing and fixing said lip portion between said retaining cap and said housing, said retaining cap having a retaining cap opening therethrough aligned with said aperture and having dimensions allowing said flexible portion of said one-way valve to extend at least partially therethrough responsive to pressure created during a cough.

6. The tracheostomy valve of claim 5, wherein the diameter of said retaining cap opening is substantially equal to the internal diameter of said aperture.

7. The tracheostomy valve of claim 5, wherein said housing further includes an exterior circumferential groove in said forward end and said retaining cap includes a portion that fits within said circumferential groove.

8. The tracheostomy valve of claim 1, wherein said first and second flexible edges are biased apart responsive to the pressure within said rear opening being substantially equal to the pressure within said forward opening.

9. The tracheostomy valve of claim 1, wherein said housing is constructed of a plastic.

* * * * *

UNITED STATES PATENT AND TRADEMARK OFFICE
CERTIFICATE OF CORRECTION

PATENT NO.   : 5,392,775
DATED        : February 28, 1995
INVENTOR(S)  : Claude N. Adkins, Jr. and Blane P. Marie It is certified that error appears in the above-identified patent and that said Letters Patent is hereby corrected as shown below:

In Column 7, Line 15, "firing" should read --fitting--.

Signed and Sealed this

Sixth Day of June, 1995

Attest:

BRUCE LEHMAN

Attesting Officer

Commissioner of Patents and Trademarks